(12) United States Patent
Hensley et al.

(10) Patent No.: US 6,352,497 B1
(45) Date of Patent: Mar. 5, 2002

(54) DETECTABLE MARKS IN TRIM MATERIAL

(75) Inventors: Robert Leo Hensley; Tanakon Ungpiyakul, both of Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/412,255

(22) Filed: Oct. 5, 1999

Related U.S. Application Data

(60) Provisional application No. 60/127,673, filed on Apr. 2, 1999.

(51) Int. Cl.[7] ................................................. B31B 1/00
(52) U.S. Cl. ................................ 493/22; 493/8; 493/10; 493/20
(58) Field of Search .............................. 493/8, 10, 11, 493/13, 19, 20, 22, 281, 373; 83/74, 76.4, 371; 156/64

(56) References Cited

U.S. PATENT DOCUMENTS

| | | | | |
|---|---|---|---|---|
| 3,986,440 A | * | 10/1976 | Macdonald et al. | 493/10 |
| 4,610,649 A | * | 9/1986 | Friess | 493/10 |
| 4,637,106 A | | 1/1987 | Bernard | 29/25.42 |
| 4,795,510 A | * | 1/1989 | Wittrock et al. | 156/64 |
| 4,837,715 A | | 6/1989 | Ungpiyakul et al. | 364/552 |
| 4,969,037 A | | 11/1990 | Poleschinski et al. | 358/106 |

(List continued on next page.)

FOREIGN PATENT DOCUMENTS

| | | | | |
|---|---|---|---|---|
| CA | 2044792 | 5/1992 | ............ | G05D/5/04 |
| EP | 0 485 691 B1 | 5/1992 | ............ | B26D/5/34 |
| EP | 485 691 A3 | 5/1992 | ............ | B26D/5/34 |
| EP | 0 657 852 A2 | 6/1995 | ............ | G06T/1/20 |
| JP | 9081233 A | 3/1997 | ........... | G05B/23/02 |
| WO | WO 93/07445 | 4/1993 | ........... | G01B/21/14 |

OTHER PUBLICATIONS

"User's Manual Model 1012," Kodak Ektapro EM Motion Analyzer, Eastman Kodak Company, pp. 1.1–7.9, 1990.
Tivin, Paul, and Thomas C. Venable, "Infrared imaging enhances manufacturing operations", Laser Focus World, pp. 107–111, Aug./Sep. 1992.
Mitsubishi, "The High & The Mighty", Product Literature, (1 sheet) 1993.
Guericke W. et al., "Rolling Operation Control Circuit— Processes the Infrared Camera Signals Fed During a rolling Operation", (1 sheet) 1997.

(List continued on next page.)

*Primary Examiner*—Peter Vo
*Assistant Examiner*—Sam Tawfik
(74) *Attorney, Agent, or Firm*—Wilhelm Law Service; Thomas D. Wilhelm

(57) ABSTRACT

This invention pertains to methods of checking for successful removal of trim material from trim areas disposed at periodic intervals along a web in a processing line. Marking material is marked, optionally as reference marks or reference images on the trim material pieces. Trim material is severed and removed to develop cut-outs at the trim areas. After removing the trim material, the method senses for the marking material at and adjacent the trim areas. The method thus detects marking material on trim material pieces which are not successfully removed from the web. In preferred embodiments, the web, outside the trim areas, is free from the specific marking material used for the reference marks or reference images. The marking material is preferably detectable, using a suitable sensor, independently of visible light emanating from, or reflected from, the marking material. Exemplary marking material can be detected using magnetic flux, energy in the ultraviolet spectrum, an olfactory sensor, color discrimination, energy in the infrared spectrum, and/or an optical brightener detectable through action of energy in the ultraviolet spectrum. The invention comprehends a web comprising corresponding trim areas, corresponding trim material, and corresponding marking material.

79 Claims, 4 Drawing Sheets

U.S. PATENT DOCUMENTS

| | | | |
|---|---|---|---|
| 5,045,135 A | 9/1991 | Meissner et al. | 156/64 |
| 5,200,023 A | 4/1993 | Gifford et al. | 156/626 |
| 5,235,515 A | 8/1993 | Ungpiyakul et al. | 364/469 |
| 5,286,543 A | 2/1994 | Ungpiyakul et al. | 428/74 |
| 5,359,525 A | 10/1994 | Weyenberg | 364/469 |
| 5,386,117 A | 1/1995 | Piety et al. | 250/330 |
| 5,388,618 A | 2/1995 | Decock | 139/1 R |
| 5,399,016 A | 3/1995 | Martin | 374/7 |
| 5,458,062 A | 10/1995 | Goldberg et al. | 101/485 |
| 5,543,177 A | 8/1996 | Morrison et al. | 427/288 |
| 5,637,871 A | 6/1997 | Piety et al. | 250/330 |
| 5,659,538 A | 8/1997 | Stuebe et al. | 364/469.02 |
| 5,733,236 A * | 3/1998 | De Smedt | 493/8 |

OTHER PUBLICATIONS

"Aquiring and Displaying Images", COGNEX, pp. 34–35, 136–138, 143, 146–148, 153–154, and 530. Date unknown.

"Before We Can Tell You What's Wrong, We'll Have To Take Your Temperature", Flir Systems, Product Literature, (1 sheet) Date unknown.

"Infrared Focal Plane Array Camera", Cincinnati Electronics, Product Literature (4 sheets) Date unknown.

Information Processing, "CVIM Configurable Vision Input Module", Product Literature (2 sheets) product available from COGNEX. Date unknown.

* cited by examiner

DETECTABLE MARKS IN TRIM MATERIAL

CROSS-REFERENCE TO RELATED APPLICATIONS

This application claims priority to Provisional Application Ser. No. 60/127,673 filed Apr. 2, 1999.

BACKGROUND

The manufacture of absorbent articles such as diapers, training pants, incontinence underwear articles, and the like, typically includes compiling and processing a web substrate as a continuous band of end-to-end or side-to-side work pieces from which respective absorbent articles are eventually derived, typically one absorbent article from each work piece. The compiling and processing includes assembling various elements to the web substrate, and shaping and configuring the thus assembled composite web substrate.

Upon completion of the various manufacturing steps, the web is severed across a transverse dimension of the web, typically across the full width of the web, to thereby separate from the web respective ones of the work pieces as separate and distinct units of absorbent article product.

During the fabrication process, the units of product become progressively defined in the work pieces until such time as the work pieces are severed from the web as separate and distinct units of product. In the web, the work pieces are generally associated with respective repeat elements on the web and the number and positioning of the respective elements in the finished units of product.

Thus, one familiar with the definition of the products to be derived from the web can, by observing the locations and repeat frequencies of respective elements on or in the web, typically perceive the identities and locations of respective ones of the work pieces on the web, and can correspondingly perceive the identities and locations of the respective units of product which will be derived from the web.

In manufacturing certain absorbent articles, trim material pieces are defined in trim areas; and the trim material pieces are severed and removed from the web. Exemplary of such trim areas are cut-outs associated with leg openings such as in, for example, diapers, training pants, incontinence underwear articles, and the like.

Successfully severing the trim material pieces from the web at the trim areas requires that the composite web material be severed about the entirety of the boundary between the trim material and the balance of the web.

Removing apparatus is typically designed for removing a trim piece that has been completely severed, and is typically not designed for completing severance where the trim piece has been only partially severed. Accordingly, successful removal of the trim pieces from the web at the trim areas is generally limited to work pieces where the corresponding web material has been completely severed from the web by the time the respective thus cut-out area, and associated trim piece, arrive at the removing station on the fabrication line.

Thus, successfully removing the trim piece depends heavily on the success of the severing step in severing the trim piece about the entirety of the boundary of the trim area with the web. When the trim piece is not completely severed, there is a high probability that the removing apparatus will not successfully remove the trim piece from the web.

Cutting apparatus typically employed in making leg cut-outs in disposable absorbent diapers periodically fails to completely sever the trim piece from the web. When that happens, the trim piece typically stays with the web, and when the respective work piece is cut from the web, the trim piece stays with the resulting unit of product, as a product defect.

SUMMARY

It is an object of the invention to provide a method of checking for or verifying successful removal of trim material from trim areas at periodic intervals along a web in a processing line fabricating discrete units of product.

It is another object to provide such a method utilizing marking material on trim material pieces, removing the trim pieces which contain the marking material, and then sensing for the marking material to detect trim pieces not successfully removed.

It is still another object to provide such method wherein the marking material on the trim pieces is distinguishable from any indicator material used on the web outside the trim areas.

Yet another object is to apply a sensor for the marking material in sufficient proximity to the web and at suitable orientation to the web, thereby checking for trim material not successfully removed.

Still another object is to provide a web including marking material, confined in the trim areas, and which can be detected by a sensor, whether by visible light, or independently of visible light utilizing, for example, magnetic flux, ultraviolet light, an olfactory sensor, infrared energy, and/or an optical brightener detectable under ultraviolet light.

A more specific object is to provide such web free from the marking material outside the trim areas, such that the sensor can distinguish marking material, on trim material not successfully removed from the web, from other indicator material which may be present on the web.

Yet another object is to provide a method wherein a sensor is effective to sense the marking material through a visually obstructive layer between the sensor and the reference marks.

A further object is to provide apparatus for checking for successful removal of trim material from a web, including a sensor in sufficient proximity to the web, and at suitable orientation to the web, to be activated by marking material which is on the trim material and which comes into sensing proximity to the sensor, thus to check for successful removal of the trim material.

A more specific object is to provide for registering the marking material to a master reference on the respective work piece.

Yet another object is to provide the marking material as marks consistent with sufficient acuity and measurable intensity, and having suitable outline, that images thereof can serve as registration marks against which other elements in the web can be registered.

A yet further specific object is to provide for registering to each other, optionally indirectly, first and second web features, at least one of which is not sufficiently sharply or distinctively defined to be readily located by a sensor.

A more specific object is to provide methods, webs, and apparatus, directed toward reliably determining whether trim material has been successfully removed from leg cut-out trim areas in absorbent personal care articles such as diapers, training pants, incontinence underwear articles, and the like.

A first family of embodiments of the invention comprehends a method of checking for successful removal of trim material from trim areas disposed at periodic intervals along a web in a processing line fabricating discrete units of product from the web, thus to develop cut-outs in the units of product at the trim areas. The method comprises utilizing marking material as images, optionally as reference marks, on trim material pieces, and severing and removing the trim material pieces thus to develop the cut-outs at the trim areas, and after removing the trim material pieces, sensing for the marking material which was on the removed trim material pieces, utilizing at least one sensor at least at and adjacent the trim areas. The method thus detects marking material on trim material pieces which have not been successfully removed from the web. The marking material as perceived by the sensor or sensors is distinguishable from any indicator material used on the web outside the trim areas.

In preferred embodiments, the web, outside the trim areas, is free from the specific marking material used for the registration and/or reference marks, thus enhancing the sensor's capacity to distinguish marking material not successfully removed from the web, from other markings or indicator material or indicia which may exist on the web.

Preferably, the marking material as applied in the trim areas is consistent with sufficient acuity and measurable intensity, and has suitable outline, that images thereof can serve as registration reference marks.

In some embodiments, the marking material as applied is consistent with sufficient acuity and measurable intensity, and has suitable outline, that the images thereof can readily be detected as registration reference marks by suitable such sensors having relatively low sensitivity and relatively low resolution capabilities, whereby low cost sensors can be successfully used in implementing the invention.

In preferred embodiments, the marking material as utilized at the trim areas is detectable using a suitable such sensor independently of visible light emanating from, or reflected from, a respective one of the reference marks. The marking material can be detected, for example and without limitation, utilizing magnetic flux, energy in the ultraviolet spectrum, an olfactory sensor, energy in the infrared spectrum, and/or an optical brightener detectable through action of energy in the ultraviolet spectrum.

Where the reference marks are to be detected using magnetic properties, the method can include creating the reference marks using magnetic ink, passing the reference marks through a magnetic field to magnetize the reference marks, and moving the magnetized reference marks past a sensor responsive to magnetic flux thus to sense the reference marks.

Methods of the invention can include generating heat selectively in the reference marks and detecting the heat using an infrared sensor, using fragrance detectable by an olfactory sensor to create the reference marks, using a dark ink sufficiently dark that the ratio of opacity of the reference mark to opacity of the web around the reference mark is no more than about 0.67/1, and including detecting or sensing for the reference mark at the trim area utilizing an optical sensor.

The composition of the marking material used in making the reference marks can include, for example, magnetic ink detectable by passing the ink through a magnetic field, fragrance detectable by an olfactory sensor, a material detectable by a sensor sensitive to energy in the ultraviolet spectrum, a material which can be activated to emit energy in the infrared spectrum, and/or an optical brightener detectable through action of energy in the ultraviolet spectrum.

Methods of the invention can further include sensing for the reference marks off-line, independently of visible light from the reference marks, after fabrication of the units of product has been substantially or fully completed.

The method further contemplates the combination of the reference marks, at least one sensor, and a controller operating in control of the fabrication line, having capacity to discern up to about 1000 of the reference marks per minute along a length of the web.

The method also contemplates distinguishing the reference marks from other material on the web on the basis of a difference between a first color of a respective reference mark and a second color of web material adjacent the reference mark.

The methods yet further contemplate culling units of product associated with trim areas wherein the at least one sensor detects a trim area reference mark downstream of the operation at which the trim material was to have been removed.

Some embodiments include utilizing at least two separate and distinct ones of the reference marks in given ones of the trim areas.

In preferred embodiments, the method contemplates removing the entirety of the marking material from the web at the severing and removing step, and after sensing for a respective reference mark at a respective cut-out, severing the web adjacent the respective cut-out and thereby creating a respective one of the discrete units of product containing the respective cut-out.

In preferred embodiments, the reference marks have leading edges sufficiently sharply-defined as to be readily discerned by suitable such sensors having relatively low sensitivity and relatively low resolution capabilities, with sufficient resolution that the reference marks can serve as reference loci to which other web elements can be registered. In such embodiments, the method further comprises applying the reference marks and a first set of web features periodically along the length of the web, using a common application device to force registration of the first set of web features to the registration reference marks.

The methods further contemplate (i) sensing timing of a respective reference mark coming into sensing proximity to a fixedly mounted such sensor, (ii) based on the timing of the reference mark coming into sensing proximity to the sensor, defining the location of a respective trim area associated with the respective reference mark, (iii) removing the trim material associated with the respective trim area according to the location of the trim area so defined, and (iv) subsequently sensing for the marking material at and adjacent the trim area to establish that the marking material has in fact been removed, and thus to establish that the respective trim material piece has been removed.

Methods of the invention can further include, after employing severing and removing apparatus to sever and remove the trim material, and after sensing for removal of the trim material, passing the trim area through the sensing zone of a metal detector or a magnetic field detector as a back-up sensor for detecting any reference mark marking material not successfully removed from the web.

In preferred embodiments, the methods contemplate utilizing a suitable sensor or sensors, in combination with a suitable composition and/or structure of marking material so as to be able to sense for the marking material through a visually obstructive layer which may be disposed between the sensor and marking material on any trim areas still on the web at the respective locations on the processing line. For example, where a trim material piece is only partially cut away from the web, and wherein an element of the trim piece is still attached to the web, however insecurely, the partially cut away piece will likely fold over as it passes along the length of the fabricating line. With the trim piece folded over, the underlying web structure/substrate, on which the marking material is applied, is positioned between the sensor and the marking material.

In preferred embodiments, the units of product comprise absorbent personal care articles, each such absorbent personal care article having ones of the cut-outs, derived from opposing sides of the web, on opposing sides of the respective personal care article.

In a second family of embodiments, the invention comprehends a method of checking for successful removal of trim material from trim areas disposed at periodic intervals along a web in a processing line fabricating discrete units of product from the web. The method comprises defining the trim areas; applying to trim material in successive ones of the trim areas, marking material as reference marks which can be detected by a sensor; removing the trim material from the respective trim areas, including removing the reference marks; and after removing the trim material, applying the sensor, in sufficient proximity to the web and at suitable orientation to the web, to the trim area to sense and detect presence of trim material not successfully removed from the respective trim area by sensing for marking material at and adjacent the respective trim areas, and thereby checking for trim material pieces not successfully removed from respective trim areas.

In a third family of embodiments, the invention comprehends a web used in fabricating discrete units of product. The web comprises trim areas, corresponding trim material in the trim areas, and marking material which can be detected by a sensor independently of visible light from the marking material, the marking material being confined in the trim areas. The web is free from the marking material outside the trim areas such that the sensor can distinguish marking material, on trim material not successfully removed from the web during a trim removal step, from other indicator material which may be present on the web.

In some embodiments, the marking material as applied being consistent with sufficient acuity and measurable intensity of reference marks, and having suitable outline, to serve as reference loci to which other web elements can be registered, and preferably to be readily so detected by a sensor having relatively low sensitivity and relatively low resolution capabilities.

Preferably, the marking material as utilized at the trim areas is detectable by action of magnetic flux such as by moving the marking material past a magnetic sensor, or by action of energy in the ultraviolet spectrum, or by action of an olfactory sensor, or by action of energy in the infrared spectrum, or through action of energy in the ultraviolet spectrum.

The marking material thus preferably comprises magnetic ink which can be detected by bringing the ink into sensing proximity with a magnetic sensor, or an optic brightener detectable by action of ultraviolet energy, or fragrance detectable by an olfactory sensor, or ink susceptible to emitting a readily detectable level of infrared energy.

In preferred embodiments, the marking material as applied to the web has sufficient acuity and measurable intensity to serve as reference images, and has suitable outline, for example leading edges sufficiently sharply-defined, as to be readily discerned by a sensor having relatively low sensitivity and relatively low resolution capabilities, with sufficient resolution that the reference images can serve as reference loci to which other web elements can be registered, and such that a suitable such sensor can preferably discern up to about 1000 of the reference images per minute along the length of the web.

In some embodiments, the web comprises at least two separate and distinct reference images each in given ones of the trim areas.

Preferred such webs of the invention comprise predominantly elements compatible with fabricating personal care absorbent articles from the web.

A fourth family of embodiments comprehends quality assurance manufacturing apparatus for checking for successful removal of trim material from areas disposed at periodic intervals along a length of a web. The apparatus comprises control apparatus including a timing system, defining the trim areas, and thereby defining the trim material to be removed from the web; marking apparatus applying, to the trim material in successive trim areas, marking material as reference marks which can be detected by a sensor; removal apparatus removing the trim material from respective trim areas, including removing the reference marks; and a sensor in sufficient proximity to the web, and at suitable orientation to the web, to be activated by the marking material applied to the trim material and coming into sensing proximity to the sensor, thus to check for successful removal of respective units of the trim material.

In some embodiments, the marking material has magnetic properties, active by the time the trim material is removed. The sensor is activated by the magnetic properties, and the quality assurance apparatus further comprises a metal detector downstream of the sensor, and operating as a secondary detector detecting magnetic properties of any marking material still on the web, or on units of product made from the web, by the time the web or respective units of product arrive at the metal detector.

The sensor is preferably adapted and configured to sense the reference marks independently of visible light from the reference marks, for example by action of magnetic flux, or by action of energy in the ultraviolet spectrum, or by action of an olfactory sensor, or by action of energy in the infrared spectrum, or through action of energy in the ultraviolet spectrum.

The apparatus can comprise a heater adapted, configured, and positioned to heat the reference marks on the fabrication line, and an infrared sensor detecting heat emanating from the so-heated reference marks.

In some embodiments, the sensor is adapted and configured to sense reference images having ratios of opacity of the image to opacity of the web around the image of no more than about 0.67/1, in which instance the sensor may be a low sensitivity and low resolution sensor.

In typical embodiments, the marking apparatus deposits on the web reference marks which, as applied, are consistent with sufficient acuity and measurable intensity of reference mark, and suitable outline, that the sensor and the control apparatus can, in combination, discern up to about 1000 of the reference marks per minute along the length of the web.

The quality assurance apparatus preferably includes a cull unit responsive to the sensor, preferably through the control apparatus, culling units of product sensed as having marking material thereon after moving past the removal apparatus.

Especially in embodiments utilizing marking material comprising significant quantities of metallic material therein, the quality assurance preferably includes a metal detector downstream of the sensor, as a back-up second sensor detecting any marking material not successfully removed from the web along with the trim material at the removing step.

In preferred embodiments, the sensor is effective to sense the marking material through a visually obstructive layer between the sensor and the reference marks.

Figure 1:
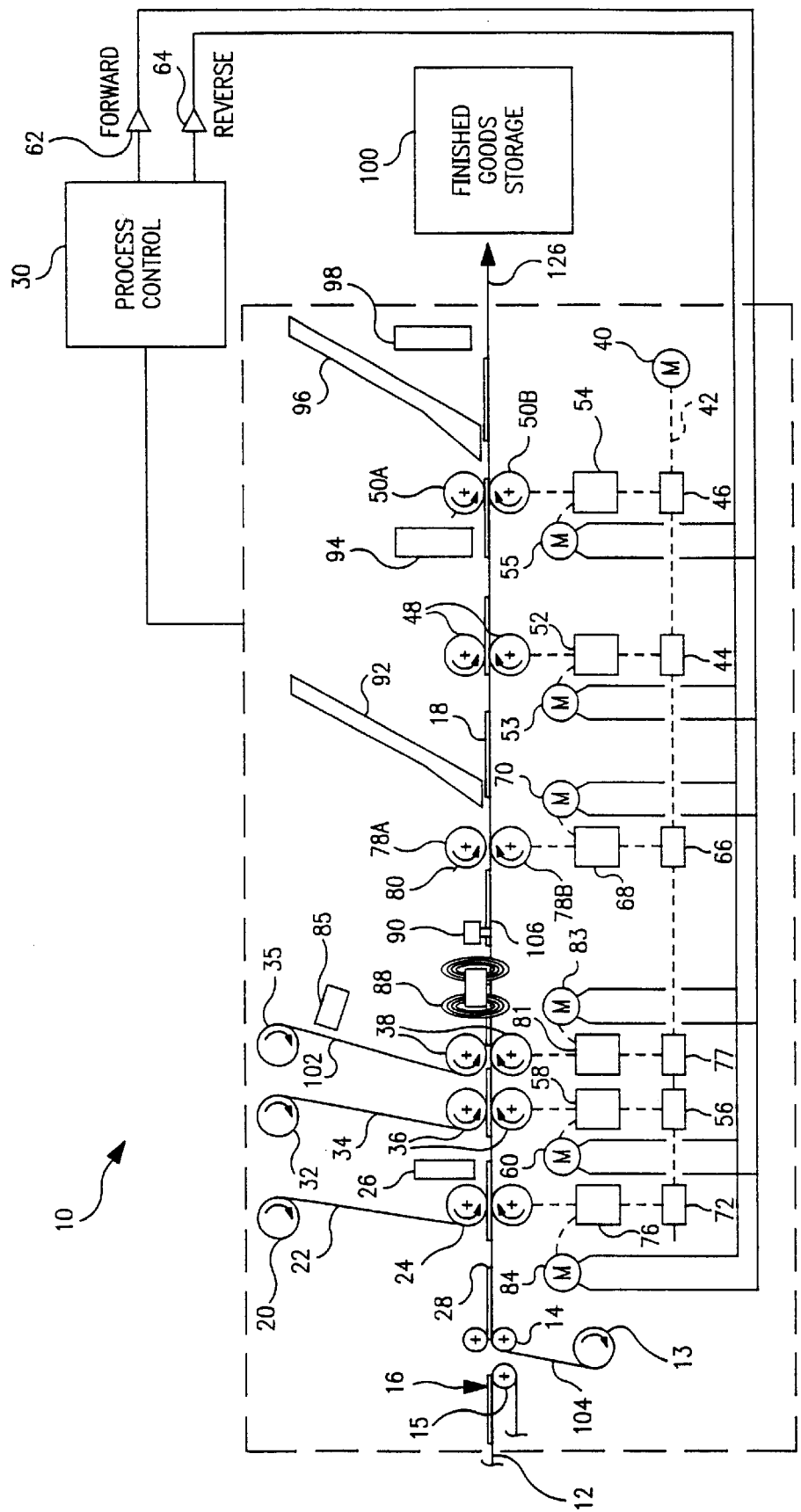
FIG. 1 shows a representational side view of a processing line illustrating methods of the invention.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

Referring to FIG. 1, absorbent article producing apparatus of the invention is illustrated schematically at 10 as a processing line, which can also be called a fabrication line. Beginning at the left end of FIG. 1, a conveyor 12, for example a vacuum conveyor, advances toward the right along the longitudinally extending manufacturing path.

Absorbent pads 16 are shown disposed on conveyor 12 at spaced intervals generally corresponding to the respective separate and distinct work pieces 18 being fabricated into absorbent articles along the processing path. Suitable elements such as outer cover, body side liner, leg cuffs, containment flaps, waist bands, and the like are placed, positioned, and otherwise combined with absorbent pads 16, or onto or into each other, at various work stations along the processing line, in the process of assembling the respective elements together to make a composite product web comprising work pieces bearing the various elements from which the absorbent articles are being made.

For example, unwind 13 supplies a body side liner web 104 to a two-roll work station 14 where underlying support of the absorbent pads is transferred from conveyor 12 at turning roll 15 to body side liner 104 at work station 14.

Unwind 20 supplies web component material such as leg elastics 22 to a two-roll work station 24 where web component material 22 is applied on, and thereby added to, body side liner 104.

Similarly, unwind 32 supplies e.g. a web of waist band material 34, whereby waist band material 34 is placed on web 12 at rolls 36.

Unwind 35 supplies a web of outer cover material 102, optionally pre-printed with a graphic 120 along the length "L" of each work piece to be defined along the processing line. Web 102 is applied over the previously assembled elements at rolls 38.

Sensor 26 is positioned between rolls 24 and rolls 36. Sensor 26 detects the leading edges 28 (FIG. 2) of absorbent pads 16 and transmits respective detect signals to process control 30.

Referring still to FIG. 1, main drive motor 40 provides the primary motive power driving the absorbent article production line. The main drive motor is employed to turn line shaft 42, coupled by gear box 44 to draw rolls 48, respectively, through differential 52 which is operated by motor 53 in response to signals from process control 30 through a forward signaling device 62 and a reverse signaling device 64, both of which are coupled to motor 53, to advance or retard the speed of draw of draw rolls 48.

Line shaft 42 is also coupled by a gear box 46 to a pair of cut-off rolls 50A, 50B, respectively, through differential 54 which is operated by motor 55 in response to signals from process control 30 through forward signaling device 62 and reverse signaling device 64, both of which are coupled to motor 55, to advance or retard the speed of cut-off rolls 50A, 50B.

Line shaft 42 is further coupled by gear box 56 to differential 58 which is operated by motor 60 in response to signals from process control 30 through forward signaling device 62 and reverse signaling device 64, both of which are coupled to motor 60, to advance or retard the speed of draw of application rolls 36, and thereby to advance or retard the speed of flow of work pieces through application rolls 36, and accordingly, the relative positioning at which waist band material 34 is applied to the work pieces.

Line shaft 42 is yet further coupled by gear box 66 to differential 68 which is operated by motor 70 in response to signals from process control 30 through signaling devices 62, 64, both of which are also coupled to motor 70, to advance or retard the relative positioning of work pieces through trim rolls 78A, 78B, and accordingly, the relative positioning of trim areas 79 which are being cut out of the work pieces as trim pieces.

Trim roll 78A includes knife 80 and thus operates as a cutting roll while operating against trim roll 78B which operates as an anvil. Trim rolls 78A, 78B thus cooperate with each other in cutting out trim material pieces 82, shown in dashed outline in FIG. 2 on opposing sides of the web. In the alternative, trim pieces 82 can be cut by high pressure water cutters (not shown) instead of mechanical knife 80 and anvil roll 78B. Suitable such water cutters are available from Flow International, Kent, Wash. USA.

Likewise, line shaft 42 is coupled by gear box 72, to differential 76 which is operated by motor 84 in response to signals from process control 30 through signaling devices 62, 64, both of which are also coupled to motor 84, to advance or retard the relative positioning of work pieces advancing through application rolls 24, and accordingly, the relative positioning, or speed of advance, of leg elastics being placed on the work pieces.

Line shaft 42 is coupled by gear box 77 to differential 81 which is operated by motor 83 in response to signals from process control 30 through signaling devices 62, 64, both of which are also coupled to motor 83, to advance or retard the relative positioning of work pieces through application rolls 38, and accordingly, the relative longitudinal positioning of the outer cover with respect to leading edges 28 of absorbent pads 16.

Additional work stations, not shown, can be employed in similar manner to place and/or affix others of the elements of the absorbent articles, directly or indirectly, onto web 12. In the same manner, line shaft 42 is coupled to respective other drive apparatus such as gear boxes and differentials as needed elsewhere along the manufacturing line in order to provide both with-machine direction and cross-machine direction drive and speed control at the various work stations.

Sensor 85 senses periodic reference marks or reference images 116 on outer cover web 102 and reports the detections of such marks to process control 30. Sensor 26 senses leading edges 28 of each pad 16 and reports the detections of the leading edges to process control 30. On the basis of the detection messages from sensors 26 and 85, process control 30 issues control signals through signaling devices 62, 64, to advance or retard the speed of advance of outer cover web 102, in order to control the positioning of reference marks 116 with respect to the leading edges of pads 16. By so using leading edge 28 as a master reference, reference marks 116 can then be used as basis for registration of, and/or for referencing, other elements of the work pieces to the leading edges of the absorbent pads.

Magnetizer 88 is illustrated downstream of application rolls 36, and upstream of cutting rolls 78A, 78B. Heating element 90, for example an electric resistance heater, is illustrated positioned between cutting rolls 78A, 78B, and magnetizer 88. Trim removal shoe 92 is disposed downstream of and adjacent trim rolls 78A, 78B. Draw rolls 48 are positioned downstream of trim rolls 78A, 78B, and upstream of cut-off rolls 50. Trim sensor 94 is downstream of trim removal shoe 92, to check that respective trim pieces have been satisfactorily removed. Cull unit shoe 96 is positioned downstream of and adjacent cut-off rolls 50A, 50B. Metal detector 98 is positioned downstream of cull unit shoe 96.

Units of product are packaged downstream of metal detector 98 in one or more packaging stations (not shown) and are then placed in finished goods storage 100 to await shipment into the distribution system.

Figure 2:
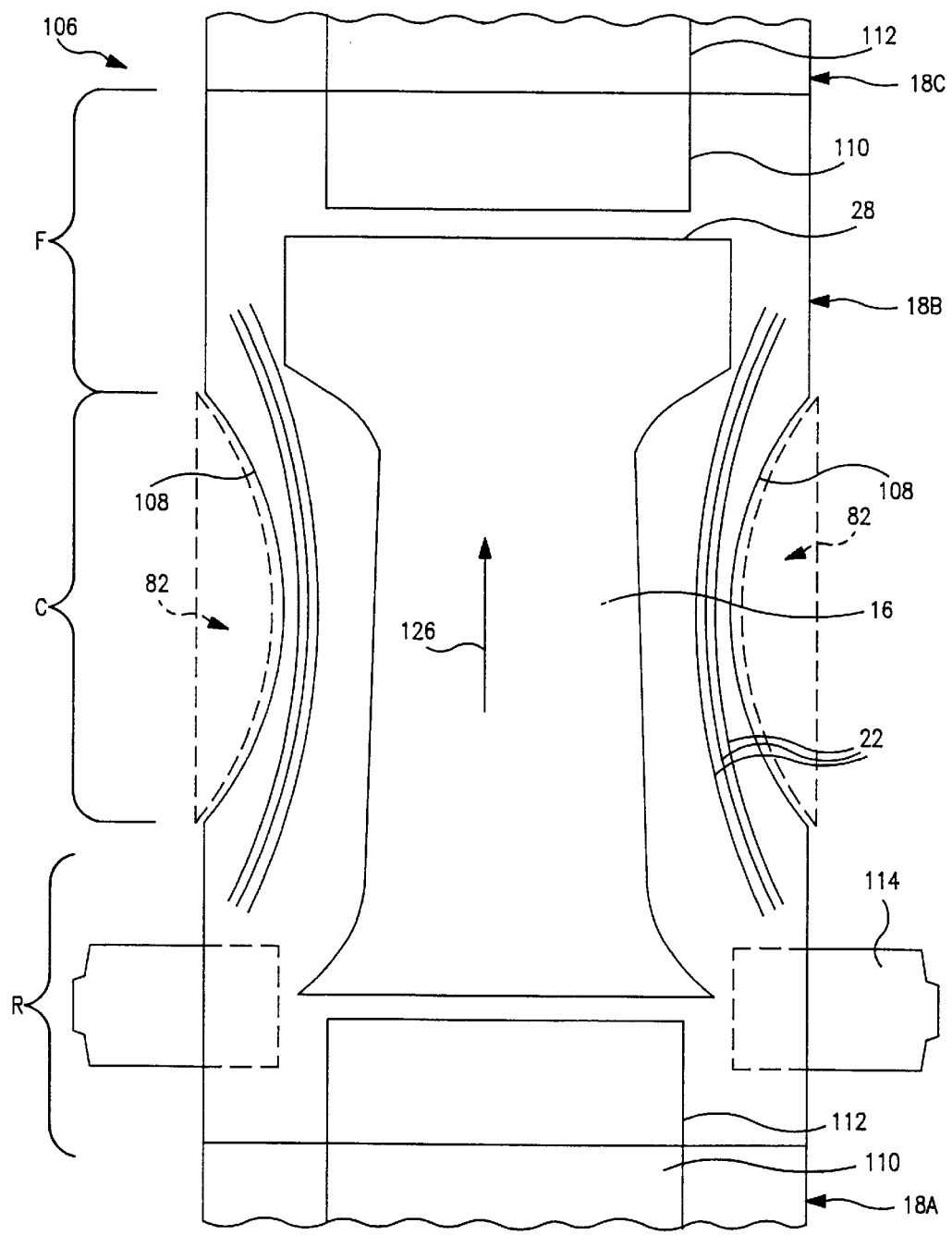
FIG. 2 shows a top view of a representative work piece in a web on the processing line of FIG. 1, connected to leading and trailing second and third work pieces.
Figure 4:
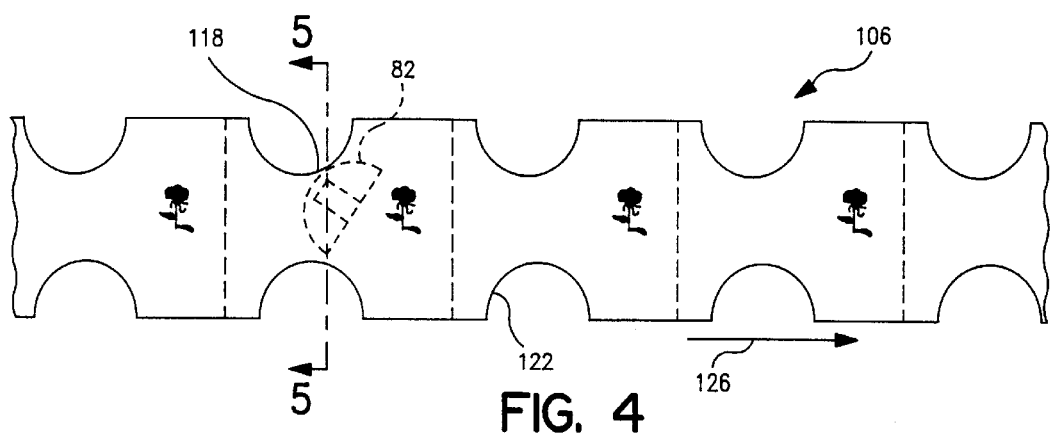
FIG. 4 shows the web of FIG. 3 after the trim pieces have been removed, and wherein one of the trim pieces remains attached, and is folded over onto the web.
Figure 5:
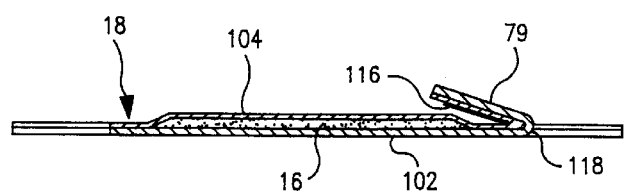
FIG. 5 shows a cross-section of the web taken at 5—5 of FIG. 4, and inverted to show the baffle side of the work piece at the bottom of the illustration.

FIGS. 2, 4, and 5 illustrate work pieces in the web, and accordingly precursors of units of product being made according to the invention. In general, an illustrated such work piece or unit of product includes a front portion "F," a rear portion "R," and a crotch portion "C" between the front and rear portions.

FIGS. 2, 4, and 5 illustrate work pieces nearing the end of the fabrication process, whereby the work pieces reasonably reflect the finished product in terms of the trim areas being removed. FIG. 2 represents the body-facing side of the work piece. FIG. 4 represents the surface of the work piece which faces away from the body of the wearer of the product, for example outer cover 102. FIG. 5 represents a cross section of the work piece at the crotch portion.

Turning now to FIGS. 2 and 5, the work piece 18 includes baffle 102 derived from baffle web 102, a body side liner 104 derived from body side liner web 104, and absorbent core 16, also known as an absorbent pad, between baffle 102 and body side liner 104. Removal of trim pieces 82 (FIG. 2) creates leg cut-outs 108 in the respective work piece. Leg elastics 22 are shown disposed between absorbent pad 16 and leg cut-outs 108. A front waist band 110 is disposed at or adjacent a leading edge of the work piece, representing the edge of the absorbent article which is disposed on the front side of the wearer's body. A rear waist band 112 is disposed at or adjacent a trailing edge of the work piece, representing the edge of the absorbent article which is disposed on the rear side of the wearer's body. Mounting ears 114, for mounting the absorbent article on a wearer, are secured to the work piece adjacent rear waist band 112 and the rear edge of absorbent pad 16.

Figure 3:
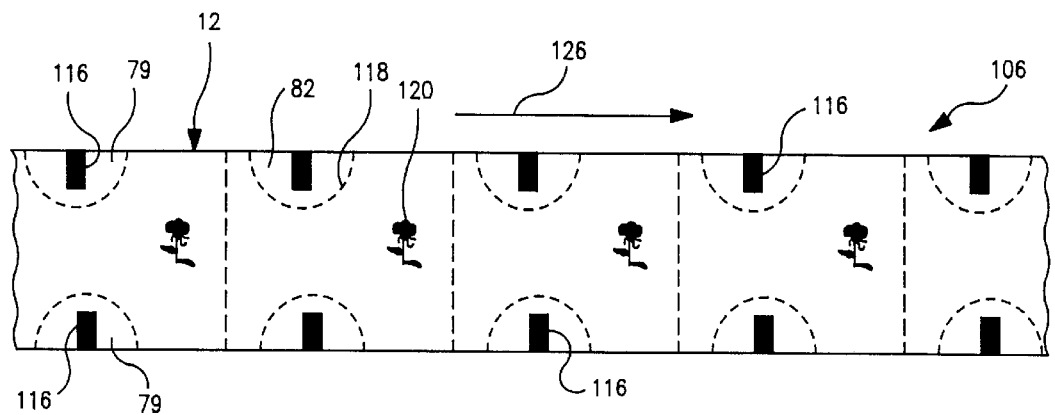
FIG. 3 is a representative top view of a continuous web being processed on the processing line, including reference marks, indicia printed on the web, and dashed outlines of trim areas.

FIGS. 2, 3, and 4, in combination, illustrate the use of detection marks, or reference marks, of the invention, which may include apertures, along with detectable work piece elements, for detecting the presence or absence of trim pieces 82 in the respective trim areas which are to become leg cut-outs 108.

When the fabrication process for fabricating absorbent articles is being set up, part of the set-up is to specify the various parameters of the units of product to be produced. Such parameters include overall dimensions of the units of product, and perimeter outlines of the units of product. In that regard, the locations of the leg cut-outs are defined in terms of the locations and configurations of trim areas, and thus the locations and configurations of trim material pieces 82 to be removed from the web in making leg cut-outs 108.

The inventors herein have addressed the costliness of not detecting trim pieces which are not properly removed. When such "not removed" trim pieces are not detected, the respective units of product may not be culled from the product line by the production apparatus, and thus may be packaged along with the units of product which are not defective.

FIG. 3 shows a length of the composite product web 106 between turning rolls 38 and cutting station 78A, 78B, including a number of work pieces, in which trim areas 79 are illustrated as having dashed lines 118 between the respective pieces of trim material 82 and the remainder of the respective work pieces. FIG. 4 shows the same length of web 106, after the web has passed trim rolls 78A, 78B such that trim pieces 82 have been removed. The dashed lines shown in FIG. 3 are typically imaginary and do not appear on web 106, though such dashed lines may be displayed on monitoring apparatus by which an operator monitors operation of the fabrication line and may, in fact, be printed on the web if desired.

Marking material is applied to web 106 inside each trim area 79 as reference marks or reference images 116 having sufficient intensity and definition, and relative opacity or other distinctiveness with respect to the adjacent background material, that the marking material can be detected by readily available sensors. The marks and images so developed generally take on the role of detection images suitable for being detected by suitable sensors. In addition or in the alternative, marks or images 116 can be used as registration reference images as further described herein.

The relative opacity of the reference mark can be expressed as the ratio of the amount of light reaching the sensor receiver when sensing the reference mark, compared to the amount of light reaching the sensor receiver when sensing background material. In order that the invention be practiced using inexpensive sensors, the relative opacity should be no greater than 0.67/1. Namely, the amount of light reaching the sensor when a reference mark is sensed is no more than 0.67 times the amount of light reaching the sensor when background material is being sensed.

When used as detection marks or images, the role of marks or images 116 is that of being readily detected, preferably including under adverse detection conditions. For example, in the second work piece from the left in FIG. 4. the respective trim piece 82 has not been completely cut-away. Rather, a small segment of the boundary at line 118 is left intact, bridging the respective trim piece 82 to the remainder of the work piece. With the trim piece 82 thus loosely attached to the work piece 18, the trim piece can flop loosely and can otherwise be moved about the connecting bridge as well as being folded and unfolded in an endless set of possible configurations.

Accordingly, the thus loosely attached trim piece can take on an endless variety of possible presentations to any sensor set up to detect the marking material in the still-attached trim piece. The primary limitation is that the trim piece is bound to the web at the bridging location where it remains attached to the rest of the work piece. The location of any such bridging material can be anywhere along the boundary of the trim area, and is not confined to the specific location, on boundary 118, which is illustrated in the drawings.

Accordingly, any sensor which is to be used to detect the presence of the trim piece, by detecting the marking material or image on the trim piece, should be able to detect the marking material at any and all locations to which the trim piece might be moved while still attached at the boundary of the trim area. In addition, the sensor should be able to detect the marking material even when one or more layers of the composite product web is positioned between the marking material and the sensor. Thus, in preferred embodiments, the detection is independent of visible light from the marking material.

Images can be detected independent of visible light where the marking material can be detected by energy that penetrates the materials typically used as parts of the work pieces. For example, in diaper fabrication, typical work pieces are elements making up baffle 102, body side liner 104, absorbent pad 16, ears 114, various elastic materials, waist bands 110 and 112, leg flaps, containment flaps, and the like.

Such elements may comprise layers covering some or all of substantially the full length and width of the main body of the diaper, or smaller portions of the diaper, as appropriate to the particular element. Such elements are generally fabricated from cellulosic and polymeric materials such as wood pulp, synthetic pulps, and thin layers of polyethylene, polypropylene, olefin copolymers, foamed and unfoamed, and the like. In addition, various spun-bonded, melt blown, and otherwise fiberized materials can be used in fabrication of various ones of the known types of absorbent articles. Further, a variety of adhesives, colorants, inks, and surfactants and other conditioning or treating materials may be employed on or in the absorbent articles.

The degree of success in detecting the presence of marks or images 116 depends on, among other factors, the cooperative relationship between the material used as the marking material and the make-up and positioning of the sensor which is used to detect the presence of the marking material. Namely, in preferred relationships, the sensor should be able to detect a parameter that does not depend on visible light for signaling detection. Accordingly, the mark or image should be able to respond to a non-visible stimulus, and/or be able to generate a non-visible stimulus, either or both of which should be able to penetrate any work piece material which may be disposed between the image and the sensor.

Such combinations of marking material and sensors can operate on the basis of, for example and without limitation, magnetic energy or infrared energy, both of which readily penetrate materials typically used in elements of absorbent articles of the type illustrated herein. Where other materials are used, other suitable energy and sensor combinations can be selected.

Magnetic such marks or images 116 can be fabricated from an ink containing magnetic materials or materials which can be made sensitive to a magnetic field, for example, ferrite particles capable of being magnetized. In some embodiments, the marking material is magnetized or otherwise activated after the marks are placed on the webs. Such ink can be, for example, a magnetic ink, K-200, having 30% by weight magnetite particles, manufactured by Flint Ink Corporation of Flint, Mich. Alternatively, other magnetic inks can be used, such as a mixture comprising a water based, suitably high remanence, low coercity, low viscosity ink having no volatile organic materials and having about 10 percent to about 80 percent by weight magnetic material.

The ink mixture should be at least about 10 percent magnetic material in order to produce a magnetic field sufficiently strong that the image can be confined to the trim area and still be detected by sensors 85 and/or 94. A higher level of magnetic material such as about 20 percent or about 30 percent by weight, is preferred whereby the image can be significantly smaller than the trim area, as illustrated in FIG. 3. Intermediate levels of magnetic material such as about 40 percent to about 50 percent by weight are preferred in some embodiments of the invention.

While higher levels of magnetic material provide for an image which has a more intense interaction with the sensor for a given surface area of the image, the requirement for sufficient fluidity of the ink, for suspension of the magnetic particles and other elements in the ink carrier fluid, and for non-magnetic solids, defines an upper limit on the maximum fraction of the magnetic material at about 80 percent by weight magnetic material.

Without limitation, such fluid ink can be further composed of, for example, a carrier liquid such as water in amount of up to about 57 percent by weight, about one percent by weight sodium tripolyphosphate, up to about 2 percent by weight surfactants, and up to about 10 percent by weight nonmagnetic solids. Preferably, the magnetic material is magnetite having an acicular particle shape, a length of about one micrometer, and an aspect ratio of about 6:1 to about 15:1; and barium ferrite having a platelet particle shape, a cross section length of about 0.4 to about 1.0 micrometer, and a thickness of less than 0.1 micrometer.

Figure 7:
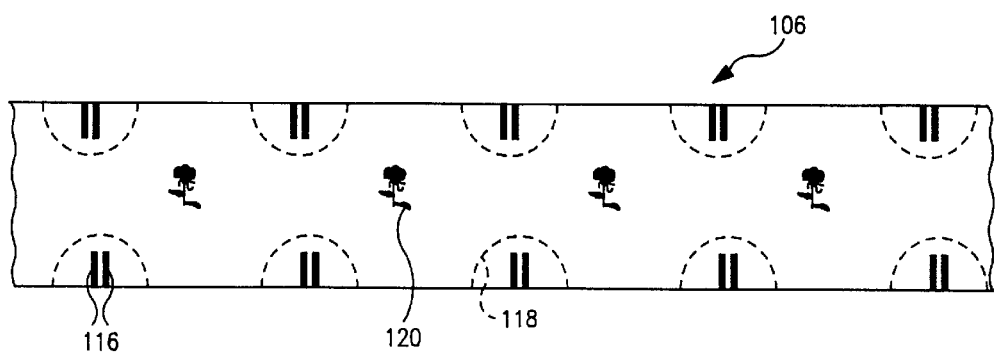
FIG. 7 is a representative top view of a continuous web as in FIG. 3 wherein the reference marks are each represented by two separate and distinct image elements.

For purposes of detecting the presence or absence of mark or image 116, thus to assess the presence or absence of trim piece 82, the size and configuration of mark or image 116 is not critical so long as the image is consistent with sufficient acuity and measurable intensity, and sharpness and size of image, as respects sensor 94, that the mark or image can readily be detected on trim piece 82. Indeed, mark or image 116 can be represented by a multiplicity of image fragments or smaller marks or images. FIG. 7 illustrates a simple representation of multiple marks or images wherein there are two marks or images in each trim area 79. In some embodiments (not shown), a segmented mark or image 116, whether continuous or discontinuous, is distributed over a large fraction of the trim area, and may be distributed over substantially the entirety of the trim area if desired, whereby any segment of trim piece 82 which is not successfully removed will likely contain at least some of the marking material, and have some corresponding prospect for being detected by sensor 94 depending on relative opacity of the marking material, the size of the image represented by the marking material and the sensitivity and resolution of the sensor. For example, if the trim piece is not all cut away, and a portion of the trim piece is subsequently torn away, the piece remaining attached may be so small that a single larger image as in FIG. 3 might have been all removed. In such case where the image has been entirely removed but a significant-sized piece of the trim material remains attached, then sensor 94, in the absence of any marking material on the trim piece would fail to perceive the trim piece, and would thus fail to recognize the defect.

On the other hand, where the marking material is distributed over the entirety of the trim material, any significant portion of trim piece left in the cut-out area will bear the marking material, whereby the sensor has some corresponding prospect for detecting the presence of the trim piece element.

Magnetizer 88 is mounted such that marks or images 116 pass through the magnetic field generated by the magnetizer. Magnetizer 88, as illustrated in FIG. 1, can represent a single magnetizer that is effective to magnetize images on both sides of the web. In the alternative, magnetizer 88 can represent a pair of magnetizers, one on each side of web 12, magnetizing the marks or images 116 on the respective sides of the web. Magnetizer 88, or respective pair of magnetizers, preferably represent permanent magnets.

In a preferred embodiment, magnetizer 88 is a Neodymium Iron Boron permanent magnet having a flux density of about 10,500 to about 12,000 gauss at the poles. Alternatively, an electromagnet can be used. In general, any magnetizing device can be used so long as the magnetizing device generates sufficient flux density to magnetize e.g. the ferrite particles in the ink, with sufficient remanence to facilitate detection of the respective images 116.

While passing through the magnetic field, the respective marks or images 116 become magnetized whereafter each such reference mark or image 116 produces a separately detectable magnetic field.

The location of magnetizer 88 is not critical to proper operation of the invention.

In the alternative, if pre-magnetized ink is used for reference marks or images 116, then no magnetizer is required.

As illustrated in FIG. 1, sensor 94 is mounted on or adjacent fabrication apparatus 10 in sufficient proximity to the web and at suitable orientation to the web, accordingly to the trim areas, to sense and detect presence of trim material not successfully removed from respective trim areas. The presence of the trim material is detected by detecting the marking material of the respective mark or image 116 on the respective trim piece, accordingly checking for trim material pieces not successfully removed from respective trim areas. Conversely, the function of sensor 94 may be expressed as verifying successful removal of trim pieces 82. The distance between sensor 94 and web 12 is exaggerated in FIG. 1 for clarity of the illustration. Sensor 94 is preferably though not necessarily mounted as close as possible to cut-off rolls 50A, 50B in order to detect only those trim pieces 82 which have not been completely removed before the respective work pieces arrive at the cut-off work station.

Since, in this embodiment, sensor 94 and marks or images 116 do not depend on visible light for successful detection, and since the sensor/image combination can operate to successfully detect images through any or all of the materials in the respective work pieces, the position of sensor 94 is not restricted to the location shown in FIG. 1, above web 106. Thus, sensor 94 can be positioned above or below web 106, regardless of whether the surface on which the image is printed is closer to the top surface of the web or closer to the bottom surface. As illustrated, images 116 are disposed on the bottom surface of web 106 in FIG. 1, while sensor 94 is above the top surface. Accordingly, sensor 94 could as well be located below the web. Further, in some embodiments, sensors corresponding to sensor 94 can be placed both above and below the web, in order to increase the success rate of actually detecting a given such still-attached trim piece 82.

Sensor 94 can be, for example and without limitation, a Hall Effect sensor, an inductive loop sensor, or a superconducting quantum interference detector, all of which are well known magnetic field sensors. Further, sensor 94 can be a fluxgate magnetometer, or a magnetoresistive element. Sensor 94 is preferably a Model GH-601 Hall Effect generator manufactured by F. W. Bell, Inc. Orlando Fla., or a Model SS94A1F analog position sensor manufactured by Honeywell Microswitch, Freeport, Ill. The operation of such sensor is well known to those skilled in the art.

The detailed description so far illustrates only applications of the invention which do not rely on visible light from the images 116. And indeed such embodiments find practical use for the purposes described above. The discussion now advances to a second benefit which accompanies certain embodiments of the invention. Namely, in such embodiments, reference marks or images 116 can also be used as registration marks for registering, to each other, certain elements on web 106 where neither element is consistent with sufficient acuity and measurable intensity, and sharpness and size of image, and/or suitable outline or relative opacity, to serve as a registration reference mark for determining relative positioning of the other element to itself.

For example, it may be desirable to register certain printed indicia on the baffle to pads 16, especially the leading edges of the pads, since leading edges 28 are used as master references on the respective work pieces, and to which all other elements of the work piece are registered. In general, two elements can be registered to each other if the locations of both of the elements can be sensed or otherwise determined with a desired level of precision. Typical registration determinations are based on the location of the leading edge of the image, namely the edge first seen by the sensor.

As desired, other locations on the work piece can be used as the master reference, for example, the trailing edge can be used as the master reference.

FIGS. 3 and 4 illustrate a flower 120 as a graphic printed on baffle 102 in each work piece. Flower 120 is defined by ink or other material significantly different from marking material which defines reference mark or image 116. While reference mark or image 116 is desirably very dark or otherwise distinctive to sensor 94, flower 120 is provided for aesthetic purposes, which are not necessarily compatible with the requirements for an easily sensed reference image. Flower 120 can be any desired color, shape, size, density, intensity, level of acuity, degree of sharpness, or the like without jeopardizing the ability to perceive its location because its location is known with respect to mark 116. In general. the dark ink required for a sharp, reliable definition of a registration reference mark is generally not desired on the finished absorbent article product, especially not in a highly visible location.

Thus, it would be very difficult to use the flower as a registration reference mark unless the characteristics of the flower were modified to make the flower more readily detectable. But that would limit, and might preclude, using flower 120 for the desired decorative purpose, or for other purposes which may be desired.

For example, in the flower of FIG. 3, the perceived location of the leading edge of the flower would be at least somewhat dependent on transverse positioning of the web. Thus, the leading edge of the flower along the length axis of the web varies, depending where along the transverse dimension of the flower, the sensor senses the leading edge. This variation in the position of the leading edge of the image along the length axis of the web can lead to false, inaccurate, and/or inconsistent position readings by the respective sensor.

In addition, the flower image is quite short along the longitudinal dimension of the web, at the stem of the flower. Such short length of image across the width of the stem, without additional image elements coming immediately thereafter for detection by sensor 94, can lead to inaccurate logic conclusions being reached by process control 30 as to the presence and/or location of the flower. Thus, flower 120 is not a good candidate for use as a registration reference mark to which another element of the web might be registered.

The commercial-grade sensors contemplated for use herein for detecting images 116 typically operate on the basis of contrast of the image to be detected against the background of the substrate around the image. Accordingly, the relative ease or difficulty of detecting a particular image is determined at least in part by the comparative intensity, such as relative opacity or other characteristic of the image compared to intensity of the same property in the surrounding material.

Where infrared energy is used in the image identity, detectability is a function of the relative intensity of infrared energy coming from the image compared to the intensity of energy coming from surrounding material. Where the image is discriminated from its background based on color, the intensity of the color difference is typically controlling of the ability to detect a particular image.

In preferred embodiments, the flowers or other indicia or graphics or the like, are printed on the baffle, namely the outer cover of the absorbent article, e.g. diaper, in registration with the definition of the length "L" of the respective work pieces (FIG. 8), in a specific location, or array of locations, along the length "L" of each work piece.

Preferred methods of the invention comprehend printing the desired pattern on the baffle in a previous step prior to assembling the various elements of the web as illustrated in FIG. 1. Thus, the printing is preferably done, and the ink dried and cured, before web 102 is mounted on the unwind from which it is fed into the processing line illustrated in FIG. 1. Correspondingly, magnetizer 88 can be employed in the printing operation if preferred, whereby the ink is magnetized as part of the printing operation.

In the instantly illustrated embodiment, it is desired to register flower 120 to leading edge 28 of pad 16 for each work piece 18, and to register images 116, through leading edge 28, with respect to cut-outs 108. As discussed above, the flower images, or other decorative image or images, are not desirable as registration references. Pad 16 presents leading edge 28 (FIGS. 1 and 2) that is readily sensed by sensor 26. However, the inability to readily sense the leading edge of flower 120 makes it difficult to register flower 120 directly to leading edge 28.

The edges of cut-outs 108 are typically not printed with easily detectable marks or images. Indeed, for absorbent articles, it is typically preferred that the edges of cut-outs 108 not be printed or that they be printed with light colored marks or images which are difficult at best to use as registration reference marks. Since the edges of the cut-outs are not printed, or are lightly printed, and since the materials used are typically either white or light colors, even if leading edge 122 represented a straight line across the width of the web, the prospects for a sensor 94, having low resolution and low sensitivity, and therefore reasonable cost, being able to reliably detect the position of leading edge 122, are not good because the comparison of the light colors against the typical white or light color background material represents insufficient contrast, whether of color wavelength or of intensity, to reliably establish a detection signal.

While such low opacity and low resolution at leading edge 122 might be reliably detectable with high resolution and high sensitivity instruments, the cost of such instrumentation would be much greater, and the detection analysis would still have to deal with the curvilinear nature of cut-outs 108. Thus, leading edge 122 of cut-out 108 is not a good candidate for use as a registration reference mark, to which another element of the web such as flower 120 might be registered. Indeed, even if more sophisticated sensors were employed, the configurations of the leading edges of both flower 120 and cut-out 108 would still make it difficult to use either flower 120 or cut-out 108 as reference marks for registration purposes.

Registering flower 120 directly to leading edge 28, or cut-out 122 directly to reference mark 116 is difficult with modestly priced instrumentation of compact size. Even if more sophisticated instrumentation were used, the ongoing reliability of such registration would be difficult to maintain. However, this invention contemplates registering flower 120 and leading edge 28 of the pad, and registering cut-out 108 to reference element 116, as follows.

In a process completed ahead of the steps illustrated in FIG. 1, flower 120 and reference mark 116 are printed onto web 102 in registration with each other on a common printing press, using the requisite distinctive marking material for marks 116, thereby achieving registration of flower 120 to reference mark 116. In the alternative, the printing of the reference marks and the flowers can be done in-line with the operation illustrated in FIG. 1. Preferably, the printing is off-line, whereby the printed web is wound up on a roll prior to being unwound and fed into the processing line illustrated in FIG. 1. In any event, the two elements are registered to each other by both being applied in a concurrent and registered printing operation wherein the two elements are registered to each other by registration of the printing steps, which create the two marks, to each other. The identity of the marking material employed, and the amount of marking material employed, in making reference marks 116 depends on the specific use intended for the respective reference marks, and the sensor or sensors to be employed in detecting the reference marks.

In the operation illustrated in FIG. 1, then, and wherein registration of flowers 120 to pads 16 is an objective of the process, web 102 as fed into the fabrication operation, carries reference marks 116 in registration with flowers 120.

Sensor 85 detects reference marks 116 and feeds the results to process control 30. Based on the inputs received from the processing line, including from sensor 85, process control 30 controls the speed of advance of web 102, thus to control registration of images 116 to leading edge 28. Registration of image 116 to leading edge 28 correspondingly operates as indirect registration of graphic 120 to leading edge 28 of pad 16, and also to cut-outs 108. Reference images 116 and leading edges 28 thus serve as intermediaries, providing for the indirect registration of graphic images 120 to pads 16, and through pads 16, to cut-outs 108, where neither the graphic 120 nor cut-outs 108 are especially desirable elements to serve as registration reference marks. Thus, physical structure of the leg cut-outs is successfully registered to printed indicia on the web albeit through two reference marks serially, without either of the physical structure or the printed indicia being desirable registration reference marks.

In view of the disclosure herein that the leg cut-outs can be successfully registered to graphics 120 through reference marks 116 and leading edges 28, it is clear that any physical element of the web can be fabricated into the web in registration with flowers 120 or cutouts 108, or any other element of the web, using suitable intermediate reference elements such as images 116 and/or leading edges 28, as registration reference in the manner described herein, for such placement. Indeed, any element whose placement can be determined with respect to reference marks 116 or leading edges 28 can be incorporated into the web in registration with any other element whose placement is or can be determined with respect to reference marks 116 or leading edge 28.

Preferred embodiments employ reference marks 116 both for detecting the presence or absence of trim material 82 and for registering flowers 120 to the master reference at leading edge 28. Thus, where the flower or other graphic is desired for placement in, for example, the rear portion of a diaper, proper registration of the graphic to the pad, in combination with registration of the cut-out to the pad, ensures proper positional relationships between the graphic, the pad, and the cut-out.

The reference marks are preferably confined inside trim areas 79 such that the cutting out of a respective trim area simultaneously (i) creates a desired new element of the work piece, namely the leg cut-out, and (ii) removes the reference mark which was used to register the graphic to the pad. See, for example, FIGS. 3, 4, and 6.

Marking materials can be, for example and without limitation, every color of the visible spectrum assuming suitable intensity of the image and contrast with material surrounding the image, can be optical brighteners which may be white or invisible in the visible spectrum such as those detectable under ultraviolet light, can be coatings that remain primarily on the surface of the web, can be coatings and other liquids that penetrate into the web, and can be materials that are easily and selectively heated. Such marking materials can be used for detecting presence of a trim piece which was not successfully removed. However, the high degree of reliability desired for such sensing step is not achieved, and thus such materials are not preferred where verifying removal of the trim piece is a high priority.

For example, a particular color can be selected and used for the marking material of reference mark 116. A sensor 94 is then used which is particularly sensitive to the selected color against the background color onto which the reference mark is printed, including any edge color at the edge of the web where the sensor is exposed to background material beside the web, such as the processing machinery, in the process of detecting the color of a reference mark 116.

Thus, where reference mark or image 116 is used primarily as a registration reference, the marking material may well be sensed in the visible spectrum, by an optical sensing system. A suitable such sensing system is available from Keyence of America, Schaumburg, Ill., as the Keyence PS56 System, including suitable transmitter, receiver, and amplifier.

A significant advantage of the invention is that, by locating reference marks 116 in an area of the work piece which is to be trimmed away, the material selected for use in the reference marks, and the size, shape, and appearance of the reference marks, can all be selected independent of the appearance requirements of the finished product, and independent of materials limitations of the finished product so long as the marking material is all trimmed away with trim material 82.

The additional freedom to so select and design reference marks 116 enables the user to better design the reference marks for ease and certainty of detection. When such product-related limitations are removed from design of the reference marks, and considering the objectives of making the marks easy to detect, the marks so designed are so large and bold, and unappealing to the eye, that they would be unacceptable on finished personal care absorbent article product.

The use of such large, bold, and objectionable marks enables the user to use the above low cost, low resolution type sensors as sensors 85, to accurately and reliably sense the positions of the respective images 116. Accordingly, the ease and reliability of registration, in combination with use of inexpensive sensors 85, is a direct benefit of locating reference marks 116 in trim areas 82, and ultimately removing the reference marks with the trim areas as part of the manufacturing process, whereby the finished product is devoid of the reference marks.

Coatings or other materials which are sensitive to ultraviolet light are typically invisible or slightly visible in the visible spectrum, and become much more detectable when exposed to ultraviolet light. Optical brighteners are well known examples of materials which are readily detectable under ultraviolet light.

Materials which are easily heated are typically dark in color such as dark colored inks, and may contain, for example, metal particles or carbon particles. When bombarded with certain types of energy such as infrared energy, such materials are readily heated, with the heating being relatively selective to the applied mark or image when compared to the remaining materials on web 12. Once heated, such materials give off the absorbed heat in the infrared spectrum whereby the presence and location of such materials can readily be detected, including through any intervening layer of material using an infrared sensor. For example, returning to FIGS. 4 and 5, a heated marking material giving off infrared energy from reference mark 116 is readily sensed and detected by an infrared sensor, including through intervening layers disposed between the sensor and the marking material.

Further, a heated reference mark can be detected by a vision imaging system such as disclosed in U.S. patent application Ser. No. 09/190,692, by Bett et al and of common assignment herewith, filed Nov. 12, 1998, herein incorporated by reference in its entirety for its teaching of infrared imaging systems and their ability to detect and manipulate infrared images, and to make adjustments to a manufacturing process on the basis of such detection instrumentation, and suitable corresponding process and control systems.

Figure 6:
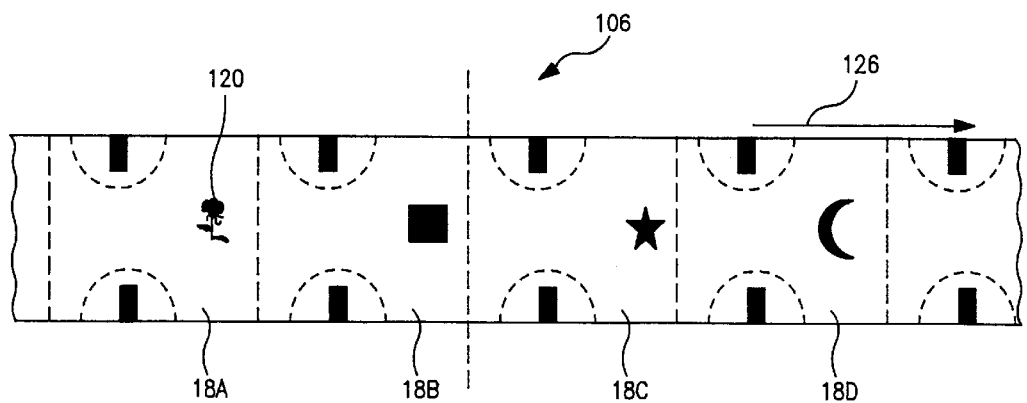
FIG. 6 is a representative top view of a continuous web as in FIG. 3, and containing different products, using registration to a common reference mark to enable fabricating multiple different products during continuous operation of the process without shutting down the processing line to set up for product changeover.

FIG. 6 illustrates a further family of embodiments of the invention. In FIG. 6, a different image is located at the location occupied by flower 120 in work piece 18A. Thus, work pieces 18B, 18C, 18D, illustrate a square, a star, and a crescent moon, respectively. In the embodiments contemplated with respect to FIG. 6, the respective image at the illustrated location on a given work piece can be varied with substantial freedom within limitations of the printing operation while maintaining the ability to register all of the respective images to mark 116, and thus to leading edge 28. For example, the four different images shown can be repeated every fourth work piece while maintaining suitable registration to each such image. Using these concepts, the respective images can each be printed in registration with respective ones of reference marks 116, and can thus be indirectly registered to leading edges 28 of respective pads 16. In this scenario, the common and consistent set of elements expressed as reference marks 116 is used to register different web elements to pads 16.

FIG. 6 illustrates the four different images on a single web 12. The invention further contemplates using a consistent such registration reference mark 116 to register different printed indicia or other elements or other marks on successive composite product webs 106. By using the common reference mark 116 on different product webs, the different products can be run on a common fabrication line without having to adjust for a different type of reference mark each time the product definition, namely the graphic, changes. Thus, the common reference mark allows the manufacturer, in certain situations, to process different products without having to convert the fabrication line set-up to accommodate for detection differences in the respective products, because each such product carries a common reference mark, suitable as a registration reference mark, against which some or all of the fabrication steps can be registered. Thus, one might make a manufacturing run fabricating only units of the flower product, followed by a manufacturing run fabricating only units of the square product, followed by a run of fabricating only units of the star product.

The description up to this point has focused on detecting certain elements of the web and/or work piece on the fabrication line. Two such functions have been discussed, namely (i) detection for the purpose of determining whether a trim piece has been removed, and (ii) detection as a mechanism for indirectly registering, to each other, two or more elements of a work piece wherein at least one element is incompatible with routinely being sensed by a commercial-grade, low cost manufacturing sensor for purpose of determining the location of the respective element.

The methods of the invention work generally as follows. Pads 16 are fed from left to right in FIG. 1 through the processing apparatus. As fed into the processing line, absorbent pads 16 are carried on vacuum conveyor 12. Pads 16 are spaced according to the lengths "L" of the work pieces, one pad to each work piece. Leg elastics 22, waist band material 34, body side liner 104, outer cover 102, and the like are assembled to each other and to pad 16 as the progressively growing composite product web 106 traverses the processing line. Reference marks 116 preferably, but not necessarily, have already been printed on outer cover 102, as marking material, prior to the outer cover entering the process steps illustrated in FIG. 1. As necessary, the marking material is activated so as to be detectable by sensor 85 for purposes of registration of position, and/or by sensor 94 for purposes of determining success of removal of trim pieces 82. Sensors 85 and 94 have been selected such that the detection properties of the sensors correspond with the activity of the marking material used in reference images 116. For example, where the marking material is magnetic, the marking material is magnetized as necessary such that the reference images are detectable by a magnetic sensor. Magnetizer 88 can be employed at any location upstream of sensor 85 or 94, as appropriate, depending on the embodiment of the process being practiced, including employment of magnetizer 88 in a prior processing operation off-line to the operation illustrated in FIG. 1.

Where marking material is to be sensed using infrared sensors 85 and/or 94, heater 90 may be employed ahead of the respective sensor or sensors in order to activate the respective reference marks 116. Where the marking material does not require activation to be sensed, then no activation apparatus need be used at the locations illustrated for magnetizer 88 and heater 90. While possible, and while fully contemplated by the invention, one would not normally employ both magnetizer 88 and heater 90 in activating a given single reference mark 116.

While it is believed that the invention has been fully disclosed above, operation of the invention is briefly illustrated below. For purposes of this illustration of the methods of the invention, it is assumed that reference mark 116 is confined to trim piece 82, and is being used both to detect removal of trim material 82 and to register indirectly graphic 120 to pad 16, whereby the reference mark is removed along with the respective trim piece 82. It is further assumed, again for illustration purposes only and without limitation, that the reference mark has a sharply defined, readily detected leading edge, extending transversely widthwise across web 12 at an angle perpendicular to the respective side edge of the web, as illustrated in, for example, FIG. 3. As reference mark 116 moves past sensor 85, sensor 85 detects the sharply defined, readily detected leading edge of the reference mark, and sends a signal to process control 30, whereupon process control 30 compares the relative positions of reference mark 116 and a corresponding pad 16, and computes the desired adjustment, if any, to line speed of web 102, in order to join image 116 to pad 16 with proper registration of image 116 and pad 16. Thus, not only is the precise location of the pad determined with respect to reference mark 116, the relative location of the pad is correspondingly indirectly fixed with respect to graphic 120, through the pre-existing registration associations of graphic 120 to image 116.

Having established the desired positional relationships between graphics 120 and pads 16, cutting rolls 78A, 78B cut away trim material 82 to produce cut-out 108 in the desired location along the length of the web. The cut out trim piece 82 is then removed by vacuum trim removal shoe 92.

Figure 8:
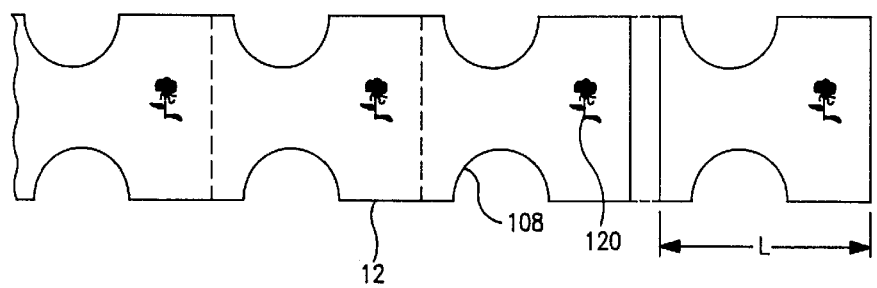
FIG. 8 is a representative top view of a continuous web as in FIG. 3, showing trim materials removed, and the leading work piece severed from the web.

As trim piece 82 is removed from trim area 79 to produce cut-out 108, the respective reference mark 116 is concurrently removed along with trim piece 82. As the work piece continues along the processing line, in the direction of arrow 126, it passes through draw rolls 48 and proceeds to sensor 94. Sensor 94 senses for presence of marking material representing the reference mark. The work piece passes through cut-off rolls 50A, 50B where the work piece is completely severed from the web and becomes a separate and distinct unit of product 128 as illustrated in FIG. 8.

If marking material was detected by sensor 94, a signal to that effect was sent to process control and instructions were sent to cull apparatus 96, whereupon cull apparatus 96 removes the unit of product from the main stream of the processing line. Cull apparatus 96 can in the alternative, simply move the cull unit of product aside laterally such as by an air blast, whereupon the culled unit can be further inspected, or manually worked to correct the defect.

If, on the other hand, the trim piece has been successfully removed at trim removal shoe 92, as desired, no marking material is found and the work piece proceeds from the cut-off rolls past the cull unit, through metal detector 98. Where the marking material is a magnetic ink or the like, metal detector 98 serves as a back-up sensor, confirming the condition sensed by sensor 94. From metal detector 98, the now fully defined and cut-off unit of product moves further along the processing line such as to packaging, not shown, thence to finished goods storage shown generally as 100 in FIG. 1.

The steps illustrated herein as being performed by centralized process control unit 30 can be performed in a more distributed manner by local process control logic built into respective ones of the machines performing various of the process steps, whereby the distributed process control is managed by process control unit 30. All such distributed logic and control is contemplated in the context of the broad scope of the invention.

The above description has focused on use of reference marks in the context of apparatus 10 on a processing line where units of product are fabricated. However, the inventors further contemplate that there are times when it is desirable to further check product in finished goods storage in order to determine and/or verify certain properties of the product, such as whether the trim material has been successfully removed from all leg cut-outs 108 in a particular population of the product. To that end, the invention contemplates using a magnetic sensor off-line, such as the sensor used at 94, to sense for magnetic material in packaged finished goods or other off-line product, without opening or otherwise disturbing any existing packaging which may be containing the product. Such sensing can be done by moving the packaged goods, in their still-sealed packages, past a respective such sensor, and sensing for magnetic material which is present only if the trim material has not been successfully removed. For purposes of this illustration, it is assumed that magnetic marking material was used for reference marks 116, and that the magnetic material was confined to trim areas 79.

In the alternative, the sensor can be moved past stationary ones of the packages of goods. Or both goods and sensor can move concurrently. In either case, such off-line sensing is tempered in the context of applying the sensor in sufficient proximity to the respective units of product and at suitable orientation to the units of product to sense and detect presence of trim material not successfully removed from the respective trim area, by detecting marking material in the respective trim material, and thereby checking off-line for trim material pieces not successfully removed from respective trim areas.

Another option for sensing for defective removal of trim material off-line is to apply fragrance to respective work pieces at the trim areas of e.g. outer cover web 102, and then to sense for the respective fragrance using a suitable olfactory sensor. As with magnetic ink, fragrance can be detected through several layers of the type of material used in personal care absorbent articles of highest current interest in the invention, whereby fragrance and respective sensors can be used in combination to detect trim pieces still in the product after the product has been placed in packaging boxes or the like.

The invention thus provides for using reference marks in trim areas to be cut-away, as indicators of the success or failure of removal of the trim pieces from the trim areas. The invention further provides for use of registration reference images as intermediaries, indirectly registering a set of web features to a master reference such as a pad while the first set of web features is not consistent with sufficient acuity and measurable intensity of image, and suitable outline, size, and intensity of contrast, to serve as registration reference mark for determining relative positioning of the set of web features with respect to a master reference.

The teaching and drawings herein illustrate the work pieces traversing the fabrication line in end-to-end, front-to-rear, relationship with each other along the length of web 12. The invention is similarly applicable to fabricating such absorbent articles which are arranged in side-by-side relationship along the length of the web.

As used herein "absorbent personal care article" and like phrases refer to a class of products worn on the body, and used generally for promotion of hygiene by the absorption of body fluids and other exudates. Examples of such absorbent articles include, without limitation, diapers, training pants, incontinence pads, feminine hygiene pads, interlabial pads, and the like.

As used herein "marking material" is a subset of "indicator material," whereby "indicator material" necessarily includes suitable "marking materials."

As used herein, "registration images," "registration reference marks," "reference images," and "reference marks" include a wide variety of materials which can be laid out in a wide variety of configurations to facilitate detection steps. Such materials include inks of every color of the visible spectrum including black and otherwise dark colors, optical brighteners such as those detectable under ultraviolet light, magnetic inks including inks that can be magnetized after being applied to the web, coatings that remain primarily on the surface of the web, coatings and other liquids that penetrate into the web, materials that are easily and selectively heated, and fragrances that can be sensed by olfactory-type sensors.

Regarding configurations, the reference images and reference marks can be applied to only a small portion, or to multiple portions, of the trim material or can be applied over a greater portion, up to the entire area defined by the trim material. Typically, a registration image is configured as a bar extending across the width of the web. However, a wide variety of configurations are contemplated, preferably in combination with the respective image being consistent with reliable, cost-effective detection by a suitably-selected sensor.

Typically, the reference image is configured with the expectation that the method of detecting the image relies at least in part on detecting a change of characteristic of the web as the leading edge of the image, such as a leading edge of a bar, moves past a sensor. In such embodiments, the leading edge of the image has a characteristic, detectable by the sensor, which contrasts distinctively with background web material immediately upstream of and/or adjacent the leading edge of the image or reference mark, such as leading up to the leading edge, such that the detectable characteristic of the reference image is readily detected by the respective sensor.

The reference image in a trim area can define a single image, or multiple images or image fragments. Any given image in a trim area 79 can be quite small, or as large as the entire surface area of the trim material, or greater. An image can be defined by straight lines or curved lines, though the leading edge is preferably a straight line perpendicular to the edge of the web. An image can be continuous or discontinuous, and can comprehend virtually any figure which can be defined within the trim area of interest.

The controller utilized in conjunction with the manufacturing process is a typical control device used for controlling web-related assemblies, programmed with suitable information regarding the size and configuration of the product, and the reference marks, so as to enable the controller, through suitable sensors, to recognize the reference marks as the marks pass the sensor.

As used herein, "web features" which are registered to the leading edges of pads 16 can take on a wide variety of identities. For example, a "web feature" can be a cut-out, a separate element assembled to a web substrate, a print mark or series of print marks such as indicia or graphic pattern or decorative element, or the like. In preferred embodiments, the "web feature" is itself a "reference element" of a print pattern for registration against the "registration image", wherein the reference element, optionally changing character between successive work pieces, repeats with sufficient frequency to be useful in establishing registration of the reference element to the cut-outs, albeit through the reference image or images.

For a web 102 bearing the reference mark, and having significant stretch capabilities along the length of the web, the reference mark e.g. 116, of the print pattern should repeat at least once for every unit of product to be made using the web. For a web 102 having little or no stretch, e.g. no more than about 20% stretch to stop, in the length of the web, the reference mark, e.g. 116, can repeat less frequently, such as every 2, 3, or 4, units of product to be made using the web. While the reference mark can be repeated even less frequently, the less the repeat frequency of the reference mark, the greater the distance between the reference mark and the e.g. graphic image and/or the greater the distance between the reference element and the master reference. The greater the above distances, the greater the prospect for error in registration, where even small amounts of stretch (e.g. 2–10% stretch to stop) are available in the web.

Accordingly, in preferred embodiments, both the e.g. graphic and the reference mark are repeated frequently along the length of the web, at least once for each unit of product to be defined in and severed from the web. Where the reference marks are repeated at such intervals or shorter intervals, the components which are referenced to each other are suitably close in space as to attenuate registration effects related to stretchability of the web in the length direction.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A method of checking for successful removal of trim material from trim areas disposed at periodic intervals along a web in a processing line fabricating discrete units of product from the web, thus to develop cut-outs in the units of product at the trim areas, the method comprising:
   (a) utilizing marking material as reference marks on trim material pieces, said reference marks being disposed inside the trim areas; and
   (b) severing and removing the trim material pieces from precursors of such units of product thus to develop the cut-outs at the trim areas of the web, and to correspondingly remove the reference marks from such precursors of such units of product; and after removing the trim material pieces, sensing for the marking material utilizing at least one sensor at least at and adjacent the trim areas, thus to detect marking material on ones of the trim material pieces which have not been successfully removed from the web, the marking material as perceived by the at least one sensor being distinguishable from any indicator material used on the web outside the trim areas.

2. A method as in claim 1, the web, outside the trim areas, being free from the marking material, thus enhancing the at least one sensor's capacity to distinguish marking material not successfully removed from the web, from other indicator material which may exist on the web.

3. A method as in claim 1, the marking material as applied being consistent with sufficient acuity and measurable intensity, and having suitable outline, that the reference marks thereof can readily be detected by a suitable such sensor having relatively low sensitivity and relatively low resolution capabilities.

4. A method as in claim 1, the marking material as applied being consistent with sufficient acuity and measurable intensity, and having suitable outline, that the reference marks thereof can readily be detected as reference images suitable for defining loci of respective reference image locations with respect to other areas on the web which are free of such reference images.

5. A method as in claim 4 wherein the reference marks have leading edges sufficiently sharply-defined as to be readily discerned by suitable such sensors having relatively low sensitivity and relatively low resolution capabilities, with sufficient resolution that the reference marks can serve as reference loci to which other web elements can be registered, the method further comprising applying the reference marks and a first set of web features periodically along the length of the web, using a common application device to force registration of the first set of web features to the reference marks.

6. A method as in claim 4 including, after sensing for a respective reference mark at a respective cut-out, severing the web and thereby creating a respective one of the discrete units of product containing the respective cut-out.

7. A method as in claim 4, including utilizing at least two separate and distinct reference marks each in given ones of the trim areas.

8. A method as in claim 4, the combination of the reference marks, the at least one sensor, and a controller operating in control of the fabrication line, having capacity to discern up to about 1000 of the reference marks per minute along a length of the web.

9. A method as in claim 4, including sensing for the reference marks off-line, independently of visible light from the reference marks, after fabrication of the units of product has been substantially completed.

10. A method as in claim 9, including using, in the reference marks, fragrance detectable by an olfactory sensor.

11. A method as in claim 9, including using, in the reference marks, magnetic ink detectable by bringing the ink into sensing proximity with a magnetic sensor.

12. A method as claim 4, the marking material as utilized at the trim areas being detectable using a suitable such sensor independently of visible light from the respective marking material images.

13. A method as in claim 4, including using a dark ink sufficiently dark that the ratio of opacity of the reference marks to opacity of the web around the reference marks is no more than about 0.67/1, and including detecting the marking material at the trim area utilizing an optical senor.

14. A method as in claim 4, including creating the reference marks using magnetic ink, passing the reference marks through a magnetic field, to magnetize the reference marks, and moving the magnetized reference marks past a sensor responsive to magnetic flux.

15. A method as in claim 14, including, after employing severing and removing apparatus to sever and remove the trim material, sensing for removal of the trim material, and passing the trim area through a sensing zone comprising one of a metal detector and a magnetic field detector as a back-up sensor for detecting any reference mark marking material not successfully removed from the web.

16. A method as in claim 4, including generating heat selectively in the reference marks, and detecting the heat using an infrared sensor.

17. A method as in claim 4, including using fragrance, detectible by an olfactory sensor, to create the reference marks.

18. A method as claim 1, including detecting the marking material at and adjacent the trim areas utilizing magnetic flux.

19. A method as in claim 1, including the marking material at and adjacent the trim areas utilizing energy in the ultraviolet spectrum.

20. A method as in claim 1, including detecting the marking material utilizing an olfactory sensor.

21. A method as in claim 1, including detecting the marking material at or adjacent the trim areas utilizing energy in the infrared spectrum.

22. A method as in claim 1, including distinguishing the reference marks on the basis of a difference between a first color of a respective reference mark and a second color of background material adjacent the reference mark.

23. A method as in claim 1, the processing line comprising a controller operating in control of the fabrication line, the method including culling units of product associated with trim areas wherein the at least one sensor detects a trim area reference mark downstream of the operation at which the trim material was to have been removed.

24. A method as in claim 1, including removing the entirety of the marking material from the web at the severing and removing step.

25. A method as in claim 1, the sensing for the marking material comprising sensing through a visually obstructive layer between the sensor and marking material on any trim areas still on the web at the respective location on the processing line.

26. A method as in claim 1, the units of product comprising absorbent personal care articles, each such absorbent personal care article having ones of the cut-outs, derived from opposing sides of the web, on opposing sides of the respective absorbent personal care article.

27. A method as in claim 1, including registering the reference marks to master references on respective work pieces in the web, and thereby indirectly registering the reference marks to the trim areas.

28. A method of checking for successful removal of trim material from trim areas disposed at periodic intervals along a web in a processing line fabricating discrete units of product from the web, thus to develop cut-outs in the units of product at the trim areas, the method comprising:

(a) utilizing marking material as reference marks on trim material pieces;

(b) registering the reference marks to master references on respective work pieces in the web, and thereby indirectly registering the reference marks to the trim areas;

(c) severing and removing the trim material pieces thus to develop the cut-outs at the trim areas; and (d) after removing the trim material pieces, sensing for the marking material utilizing at least one sensor at least at or adjacent the trim areas, thus to detect marking material on ones of the trim material pieces which have not been successfully removed from the web;

the marking material as perceived by the at least one sensor being distinguishable from any indicator material used on the web outside the trim areas.

29. A method as in claim 28, the web, outside the trim areas, being free from the marking material, thus enhancing the at least one sensor's capacity to distinguish marking material not successfully removed from the web, from other indicator material which may exist on the web.

30. A method as in claim 28, the marking material as applied being consistent with sufficient acuity and measurable intensity, and having suitable outline, that the reference marks thereof can readily be detected by a suitable such sensor having relatively low sensitivity and relatively low resolution capabilities.

31. A method as in claim 28, the marking material as applied being consistent with sufficient acuity and measurable intensity, and having suitable outline, that the reference marks thereof can readily be detected as reference images suitable for defining loci of respective reference image locations with respect to other areas on the web which are free of such reference images.

32. A method as in claim 31, the marking material as utilized at the trim areas being detectable using a suitable such sensor independently of visible light from the respective marking material images.

33. A method as in claim 31, including using a dark ink sufficiently dark that the ratio of opacity of the reference marks to opacity of the web around the reference marks is no more than about 0.67/1, and including detecting the marking material at the trim area utilizing an optical sensor.

34. A method as in claim 31, including creating the reference marks using magnetic ink, passing the reference marks through a magnetic field, to magnetize the reference marks, and moving the magnetized reference marks past a sensor responsive to magnetic flux.

35. A method as in claim 34, including, after employing severing and removing apparatus to sever and remove the trim material, and after sensing for removal of the trim material, passing the trim area through a sensing zone comprising one of a metal detector and a magnetic field detector as a back-up sensor for detecting any reference mark marking material not successfully removed from the web.

36. A method as in claim 31, including generating heat selectively in the reference marks, and detecting the heat using an infrared sensor.

37. A method as in claim 31, including using fragrance, detectible by an olfactory sensor, to create the reference marks.

38. A method as in claim 31, including sensing for the reference marks off-line, independently of visible light from the reference marks, after fabrication of the units of product has been substantially completed.

39. A method as in claim 38, including using, in the reference marks, magnetic ink detectable by bringing the ink into sensing proximity with a magnetic sensor.

40. A method as in claim 38, including using, in the reference marks, fragrance detectable by an olfactory sensor.

41. A method as in claim 31, the combination of the reference marks, the at least one sensor, and a controller operating in control of the fabrication line, having capacity to discern up to about 1000 of the reference marks per minute along a length of the web.

42. A method as in claim 31, including utilizing at least two separate and distinct reference marks each in given ones of the trim areas.

43. A method as in claim 31 including, after sensing for a respective reference mark at a respective cut-out, severing the web adjacent the respective cut-out and thereby creating a respective one of the discrete units of product containing the respective cut-out.

44. A method as in claim 31 wherein the reference marks have leading edges sufficiently sharply-defined as to be readily discerned by suitable such sensors having relatively low sensitivity and relatively low resolution capabilities, with sufficient resolution that the reference marks can serve as reference loci to which other web elements can be registered, the method further comprising applying the reference marks and a first set of web features periodically along the length of the web, using a common application device to force registration of the first set of web features to the reference marks.

45. A method as in claim 28, including detecting the marking material at and adjacent the trim areas utilizing magnetic flux.

46. A method as in claim 28, including detecting the marking material at and adjacent the trim areas utilizing energy in the ultraviolet spectrum.

47. A method as in claim 28, including detecting the marking material utilizing an olfactory sensor.

48. A method as in claim 28, including detecting the marking material at and adjacent the trim areas utilizing energy in the infrared spectrum.

49. A method as in claim 28, including distinguishing the reference marks on the basis of a difference between a first color of a respective reference mark and a second color of background material adjacent the reference mark.

50. A method as in claim 28, the processing line comprising a controller operating in control of the fabrication line, the method including culling units of product associated with trim areas wherein the at least one sensor detects a trim area reference mark downstream of the operation at which the trim material was to have been removed.

51. A method as in claim 28, including removing the entirety of the marking material from the web at the severing and removing step.

52. A method as in claim 28, the sensing for the marking material comprising sensing through a visually obstructive layer between the sensor and marking material on any trim areas still on the web at the respective location on the processing line.

53. A method as in claim 28, the units of product comprising absorbent personal care articles, each such absorbent personal care article having ones of the cut-outs, derived from opposing sides of the web, on opposing sides of the respective absorbent personal care article.

54. A method of checking for successful removal of trim material from trim areas disposed at periodic intervals along a web in a processing line fabricating discrete units of product from the web, thus to develop cut-outs in the units of product at the trim areas, the method comprising:

(a) utilizing marking material as reference marks on trim material pieces;

(b) severing and removing the trim material pieces thus to develop the cutouts at the trim areas; and (c) after removing the trim material pieces, sensing for the marking material utilizing at least one sensor at least at and adjacent the trim areas, thus to detect marking material on ones of the trim material pieces which have not been successfully removed from the web, the marking material as applied being consistent with sufficient acuity and measurable intensity, and having suitable outline, that the reference marks therof can readily be detected by the at least one sensor as reference images suitable for defining loci of respective reference image locations with respect to other areas on the web which are free of such reference images.

55. A method as in claim 54, the web, outside the trim areas, being free from the marking material, thus enhancing the at least one sensor's capacity to distinguish marking material not successfully removed from the web, from other indicator material which may exist on the web.

56. A method as in claim 54, the marking material as applied being consistent with sufficient acuity and measurable intensity, and having suitable outline, that the reference marks thereof can readily be detected by a suitable such sensor having relatively low sensitivity and relatively low resolution capabilities.

57. A method as in claim 54, the marking material as utilized at the trim areas being detectable using a suitable such sensor independently of visible light from the respective marking material images.

58. A method as in claim 54, including detecting the marking material at and adjacent the trim areas utilizing magnetic flux.

59. A method as in claim 54, including detecting the marking material at and adjacent the trim areas utilizing energy in the ultraviolet spectrum.

60. A method as in claim 54, including detecting the marking material utilizing an olfactory sensor.

61. A method as in claim 54, including detecting the marking material at and adjacent the trim areas utilizing energy in the infrared spectrum.

62. A method as in claim 54, including using a dark ink sufficiently dark that the ratio of opacity of the reference marks to opacity of the web around the reference marks is no more than about 0.67/1, and including detecting the marking material at the trim area utilizing an optical sensor.

63. A method as in claim 54, including creating the reference marks using magnetic ink, passing the reference marks through a magnetic field, to magnetize the reference marks, and moving the magnetized reference marks past a sensor responsive to magnetic flux.

64. A method as in claim 63, including, after employing severing and removing apparatus to sever and remove the trim material, and after sensing for removal of the trim material, passing the trim area through a sensing zone comprising one of a metal detector and a magnetic field detector as a back-up sensor for detecting any reference mark marking material not successfully removed from the web.

65. A method as in claim 54, including generating heat selectively in the reference marks, and detecting the heat using an infrared sensor.

66. A method as in claim 54, including using fragrance, detectible by an olfactory sensor, to create the reference marks.

67. A method as in claim 54, including sensing for the reference marks off-line, independently of visible light from the reference marks, after fabrication of the units of product has been substantially completed.

68. A method as in claim 67, including using, in the reference marks, magnetic ink detectable by bringing the ink into sensing proximity with a magnetic sensor.

69. A method as in claim 67, including using, in the reference marks, fragrance detectable by an olfactory sensor.

70. A method as in claim 54, including distinguishing the reference marks on the basis of a difference between a first color of a respective reference mark and a second color of background material adjacent the reference mark.

71. A method as in claim 54, the combination of the reference marks, the at least one sensor, and a controller operating in control of the fabrication line, having capacity to discern up to about 1000 of the reference marks per minute along a length of the web.

72. A method as in claim 54, the processing line comprising a controller operating in control of the fabrication line, the method including culling units of product associated with trim areas wherein the at least one sensor detects a trim area reference mark downstream of the operation at which the trim material was to have been removed.

73. A method as in claim 54, including utilizing at least two separate and distinct reference marks each in given ones of the trim areas.

74. A method as in claim 54, including removing the entirety of the marking material from the web at the severing and removing step.

75. A method as in claim 54 including, after sensing for a respective reference mark at a respective cut-out, severing the web adjacent the respective cut-out and thereby creating a respective one of the discrete units of product containing the respective cut-out.

76. A method as in claim 54 wherein the reference marks have leading edges sufficiently sharply-defined as to be readily discerned by suitable such sensors having relatively low sensitivity and relatively low resolution capabilities, with sufficient resolution that the reference marks can serve as reference loci to which other web elements can be registered, the method further comprising applying the reference marks and a first set of web features periodically along the length of the web, using a common application device to force registration of the first set of web features to the reference marks.

77. A method as in claim 54, the sensing for the marking material comprising sensing through a visually obstructive layer between the sensor and marking material on any trim areas still on the web at the respective location on the processing line.

78. A method as in claim 54, the units of product comprising absorbent personal care articles, each such absorbent personal care article having ones of the cut-outs, derived from opposing sides of the web, on opposing sides of the respective absorbent personal care article.

79. A method as in claim 54, including registering the reference marks to master references on respective work pieces in the web, and thereby indirectly registering the reference marks to the trim areas.

* * * * *